United States Patent [19]

MacKew

[11] 3,977,408

[45] Aug. 31, 1976

[54] PROSTHETIC CATHETER

[76] Inventor: Allan H. MacKew, 1634 Willow Drive, Sandusky, Ohio 44870

[22] Filed: Nov. 1, 1974

[21] Appl. No.: 520,854

[52] U.S. Cl. .................... 128/349 B; 128/DIG. 26
[51] Int. Cl.² ........................................ A61M 25/00
[58] Field of Search ...... 128/349 B, 349 BV, 350 R, 128/344, 325, 351, 246, DIG. 26

[56] References Cited

UNITED STATES PATENTS

| | | | |
|---|---|---|---|
| 550,238 | 11/1895 | Allen | 128/246 |
| 1,763,079 | 6/1930 | Zacsek | 128/246 |
| 1,922,084 | 8/1933 | Gerow | 128/349 B |
| 2,159,947 | 5/1939 | Gansel | 128/349 R |
| 2,547,758 | 4/1951 | Keeling | 128/349 B |
| 2,642,874 | 6/1953 | Keeling | 128/349 B |
| 2,936,760 | 5/1960 | Gants | 128/349 B |
| 3,394,705 | 7/1968 | Abramson | 128/349 B |

FOREIGN PATENTS OR APPLICATIONS

| | | | |
|---|---|---|---|
| 363,505 | 11/1922 | Germany | 128/349 R |

*Primary Examiner*—Dalton L. Truluck
*Attorney, Agent, or Firm*—Mason, Fenwick & Lawrence

[57] ABSTRACT

A system for enabling the injection of liquid into the prostate is disclosed consisting of an elongated tubular catheter member formed of flexible material of sufficient rigidity and a sufficiently small outer diameter to enable insertion along the length of the male urethra through the cystouretheral junction into the bladder; inflatable balloon means is provided adjacent the proximal end capable of inflation by a conduit extending along the length of the tubular catheter to a size sufficiently large to prevent removal of said balloon means from the bladder; a medication providing conduit also extends along the length of said elongated tubular member with a medication dispensing duct means communicating with the said medication providing conduit, said medication dispensing duct being spaced outwardly along the length of said tubular member a distance from said balloon means so as to be positioned adjacent the area of the prostate in which the prostatic ducts are located when the balloon is in place and engaged with the inner wall of the bladder adjacent the cystouretheral junction to permit medication from said medication providing conduit to be injected into the prostate.

1 Claim, 5 Drawing Figures

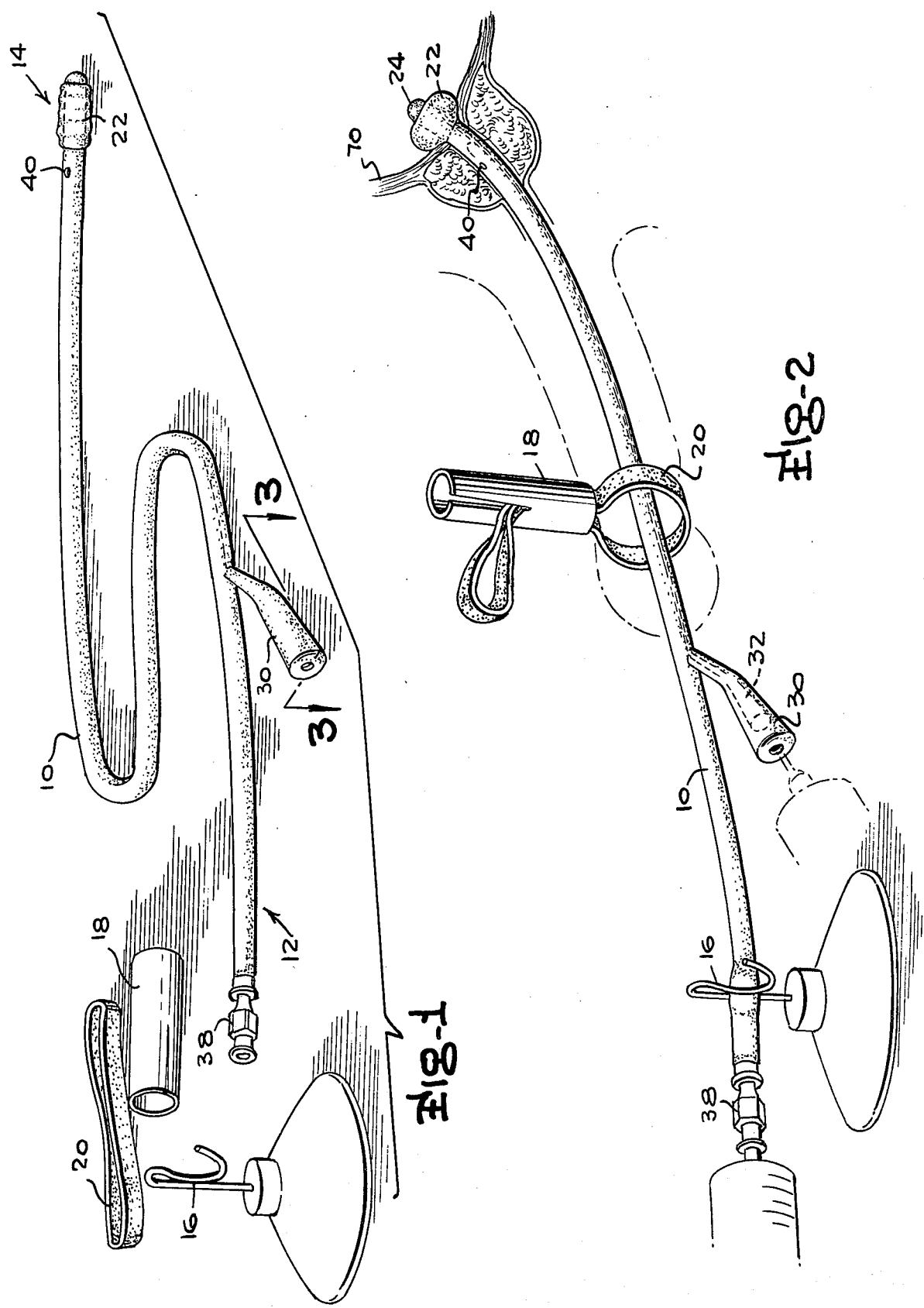

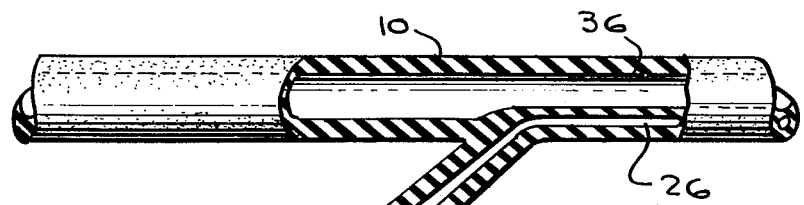
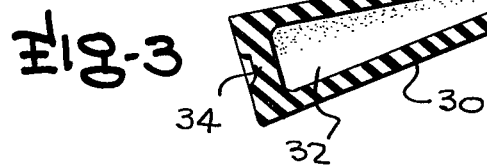
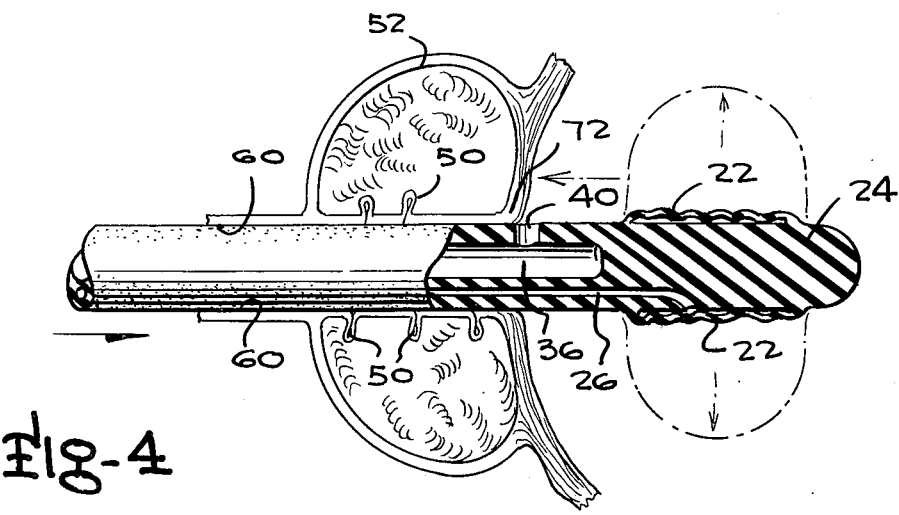
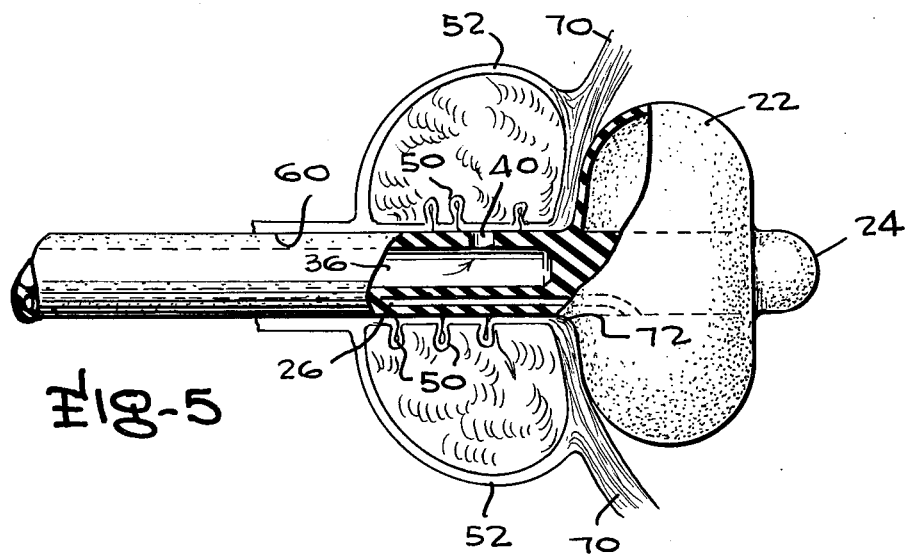

PROSTHETIC CATHETER

This invention is in the field of medication dispensing means and is specifically directed to the field of catheters and is more specifically directed to a urinary tract type catheter capable of injecting medication into the human prostate gland.

It is initially noted that the word "medication" as used herein is used in its broadest sense and can be a radio-opaque diagnostic liquid for use in enabling x-ray or flouroscopic examination of the patient or it can be an antibiotic or other direct treatment material. In any event, treatment and/or examination of the human prostate is an extremely difficult matter due to the inaccessible location and small size of the prostate which makes it difficult to locate and treat. Moreover, the only access to the prostate is through the prostatic ducts communicating with the urethra a small distance outwardly from the junction of the prostate with the bladder wall.

Examination of the prostate by means of x-ray equipment has not been possible prior to the present invention due to the fact that there has been no known way in which radio-opague material could be injected into the prostate to enable the employment of x-rays for ascertaining the shape and size of the prostate gland. Moreover, treatment of prostatitis by use of antibiotics has not been effectuable by direct application to the prostate, but has been limited largely to oral dosage or hypodermic injection, neither of which has always provided a satisfactory amount of antibiotic material to the interior of the prostate.

The foregoing and other problems have created a longstanding need for a means capable of injecting medication into the prostate via the prosthetic duct. However, the present invention represents the first successful device capable of achieving the foregoing function.

Therefore, it is the primary object of the present invention to provide a new and improved catheter.

Yet another object of the present invention is the provision of a new and improved catheter capable of providing medication to the prostate.

Achievement of the foregoing objects is enabled by the preferred embodiment of the invention which comprises an elongated catheter consisting of a flexible tubular member having a distal end and a proximal end. The flexible tubular member is formed of rubber or similar material having sufficient rigidity and a sufficiently small outer diameter to permit insertion along the length of the male urinary tract so that the proximal end is positioned in the interior of the bladder. The insertion end of the tubular member includes an inflatable balloon means of annular shape spaced a slight distance outwardly from the innermost extent of a solid tip portion and an inflation enabling conduit extends along the length of the catheter and has its inner end connected to the balloon and its outer end connectable through an offset fitting to a hypodermic or other source of air capable of inflating the annular balloon member. Inflation of the annular balloon member prevents extraction of the catheter from within the confines of the bladder and also enables an exact positioning of a medication providing duct adjacent the prostatic ducts to enable forced injection of medication through the prostatic ducts into the interior of the prostate.

Additionally, the catheter is provided with a medication providing conduit extending along its length and having an inner end in communication with the medication dispensing duct extending through the wall of the catheter. The medication dispensing duct is accurately positioned outwardly from the inflatable balloon member a sufficient distance that the medication dispensing duct is in the area of the prostatic ducts when the balloon member is inflated and moved outwardly against the inner wall of the bladder. Consequently, the medication dispensing duct is accurately positioned in alignment with the prostatic duct and the injection of medication along the length of the medication providing conduit results in the injection of the medication through the prostatic duct into the prostate interior. Escape of the medication from the external area of the catheter outwardly along the length of the urethra is prevented by the employment of a penis clamp operable for moving the urethra into sealing contact with the outer surface of the catheter. Similarly, the balloon member on the interior of the bladder serves to prevent the medication from escaping into the bladder due to the fact that the annular balloon member is forcefully engaged with the junction of the urethra and the bladder. Consequently, medication injected under pressure can only flow into the prostate so that the subject invention enables the achievement of hitherto unachievable results in a uniquely simple and effective manner.

A better understanding of the manner in which the objects of the invention are achieved will be enabled when the following written description is considered in conjunction with the appended drawings in which:

FIG. 1 is a perspective view of the component parts of the preferred embodiment;

FIG. 2 is a perspective view illustrating the preferred embodiment in use in position for injecting medication into the prostate;

FIG. 3 is a sectional view taken along lines 3—3 of FIG. 1;

FIG. 4 is an enlarged view partially in section of the inner end of the preferred embodiment following positioning of same on the interior of the bladder but prior to inflation of the balloon member; and FIG. 5 is similar to FIG. 4 but illustrates the balloon member in inflated position engaging the wall of the bladder for enabling the injection of medication into the interior of the prostate.

Turning first to FIG. 1, the preferred embodiment comprises a catheter consisting of an elongated tubular member 10 formed of rubber or other suitable flexible material and having a distal end 12 and a proximal end 14. Additionally, the inventive system employs a holding clamp 16 for clamping the distal end of the tube 10 and a penis clamp consisting of a slotted tube 18 and a rubber band 20 which can be employed for effecting a clamping operation shown in FIG. 2.

An annular inflatable balloon means 22 extends about the outer periphery of a solid tip portion 24 on the proximal end of the catheter member. It is to be noted that the annular balloon 22 is spaced outwardly a small distance from the extreme proximal end of the solid tip portion 24 as best shown in FIGS. 4 and 5.

A relatively small inflation enabling conduit 26 extends along the length of the elongated flexible member and has its innermost end in communication with the interior of the annular inflatable balloon member 22 as best illustrated in FIG. 4. The distal end of the inflation enabling conduit 26 extends outwardly through a fitting 30 having a hollow interior chamber 32 capable of receiving a hypodermic needle through a wall portion 34 as illustrated in phantom in FIG. 2.

Additionally, the elongated tubular member 10 includes a medication providing conduit 36 of substantially greater size than the inflation enabling conduit 26 which has its distal end open for receipt of a hypodermic needle 38 or the like for the provision of medication.

A medication dispensing duct 40 extends through the wall of the conduit at a location spaced outwardly from the annular inflatable member 22 a distance so that the duct 40 will be in the area of alignment with the prostatic duct 50 of the prostate 52 when the apparatus is used in its intended manner.

In use, the inventive apparatus is initially inserted along the length of the urethra 60 so that the tip portion 24 and the annular inflatable balloon 22 are on the interior of the bladder 70. The annular inflatable balloon 22 is then inflated to the dotted line position of FIG. 4 and the catheter is moved outwardly from the FIG. 4 position until the balloon engages the wall of the bladder 70 as shown in FIG. 5. Engagement of the balloon with the wall of the bladder fixedly positions the medication dispensing duct 40 with respect to the prostatic ducts 50 and subsequent injection of dye or other medication along the medication providing conduit 36 results in injection of such medication into the interior of the prostate. Use of the clamp means 18, 20 etc, prevents the medication from escaping outwardly along the length of the urethra and engagement of the bladder wall of the balloon 22 prevents the medication from escaping into the bladder. Clamp 16 holds the tubular member in a taut condition as illustrated in FIG. 2 so that balloon 22 is maintained in forceful contact with the wall of the bladder. Consequently, the pressure of the medication can reach a level sufficient to cause flow of the medication into the prostate.

Therefore, it will be seen that the subject invention meets a hitherto unmet need and represents a significant advance in the art. While numerous modifications of the preferred embodiment will undoubtedly occur to those of skill in the art, it should be understood that the spirit and scope of the invention is to be limited solely by the appended claims.

I claim:

1. A system for enabling the injection of liquid into the prostate comprising a catheter consisting of an elongated tubular member having an external end and an insertion end formed of flexible material of sufficient rigidity and a sufficiently small outer diameter to enable insertion along the length of the male urethra through the cystourethral junction into the bladder, inflatable balloon means adjacent the insertion end of said elongated tubular member capable of inflation to a size sufficiently large to prevent removal of said balloon means from the bladder, an inflation enabling conduit extending along the length of said elongated tubular member and having an inner end communicating with the interior of said balloon means and an outer end connectable to a source of gas for enabling inflation of said balloon means, a medication providing conduit also extending along the length of said elongated tubular member, medication dispensing duct means in said tubular member communicating with the insertion end of said medication providing conduit, said medication dispensing duct being spaced outwardly along the length of said tubular member a distance from said balloon means so as to be positioned adjacent the area of the prostate in which the prostatic ducts are located when said balloon is in place and engaged with the inner wall of the bladder adjacent the cystourethral junction to permit medication from said medication providing conduit to be injected into the prostate, penis clamp means for clamping the urethra to the outer surface of said elongated tubular member in an area outwardly of said medication duct means and a holding clamp mounted on a support spaced from the patient for clamping the external end of the elongated tubular member for holding said elongated tubular member in tension when positioned in a patient to maintain said balloon in position in forceful engagement with the inner wall of the patient's bladder with sufficient force to permit medication to be injected in the portion of the urethra between the balloon and the penis clamp means at sufficient pressure to enable flow of the medication into the prostate via the prostatic ducts.

* * * * *